(12) United States Patent
Lee et al.

(10) Patent No.: US 9,598,288 B2
(45) Date of Patent: Mar. 21, 2017

(54) METHOD FOR PREPARING ZINC-HISTIDINE SELF-ASSEMBLY BIOMIMETRIC COMPLEX, ZINC-HISTIDINE SELF-ASSEMBLY COMPLEX PREPARED BY SAID METHOD, AND METHOD FOR REDUCING CARBON DIOXIDE USING SAID ZINC-HISTIDINE SELF-ASSEMBLY COMPLEX

(71) Applicant: INDUSTRY-ACADEMIC COOPERATION FOUNDATION YONSEI UNIVERSITY, Seoul (KR)

(72) Inventors: Sang-Yup Lee, Seoul (KR); Min-Chul Kim, Siheung-si (KR); Yu-Kyoung Lee, Gwangju (KR); Sunhyung Kim, Gunpo-si (KR); Jinyoung Kwak, Seoul (KR); Youngjoon Lim, Seoul (KR); Sangwoo Park, Daejeon (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 236 days.

(21) Appl. No.: 14/456,106

(22) Filed: Aug. 11, 2014

(65) Prior Publication Data
US 2015/0151974 A1 Jun. 4, 2015

(30) Foreign Application Priority Data
Dec. 3, 2013 (KR) .................. 10-2013-0149435

(51) Int. Cl.
*C01B 31/24* (2006.01)
*C07F 3/06* (2006.01)

(52) U.S. Cl.
CPC ............... *C01B 31/24* (2013.01); *C07F 3/06* (2013.01)

(58) Field of Classification Search
CPC ........ C01B 31/24; C07F 3/06; A61K 31/4172
See application file for complete search history.

(56) References Cited

U.S. PATENT DOCUMENTS

| 8,138,370 B2 | 3/2012 | Hirata | |
|---|---|---|---|
| 2014/0234946 A1* | 8/2014 | Constantz | ............... C01B 31/24 435/266 |

FOREIGN PATENT DOCUMENTS

| KR | 10-2011-0087273 A | 8/2011 |
|---|---|---|
| KR | 10-1163964 B1 | 7/2012 |

(Continued)

OTHER PUBLICATIONS

English machine translation of KR10-1163964B1.*
(Continued)

*Primary Examiner* — Richard M Rump
(74) *Attorney, Agent, or Firm* — LRK Patent Law Firm

(57) ABSTRACT

Method for preparing zinc-histidine self-assembly biomimetic complex activating reaction to convert carbon dioxide into bicarbonate ion, zinc-histidine self-assembly biomimetic complex by preparation method, and method for reducing carbon dioxide using zinc-histidine self-assembly biomimetic complex. The preparation includes: mixing L-histidine and p-toluene sulfonic acid in first organic solvent to form first mixed solution and recrystallizing first mixed solution with ethyl ether to prepare first mixed substance; mixing first mixed substance with azelaic acid in second organic solvent to form second mixed substance containing imidazole and amide groups; mixing second mixed substance with NaOH and HCl in third organic solvent to form third mixed solution and recrystallizing third mixed solution with ethyl ether to prepare third mixed substance having amphiphilic characteristic; and mixing third mixed substance with aqueous solution of zinc precur- (Continued)

sor and causing self-assembly to prepare zinc-containing self-assembly biomimetic complex.

11 Claims, 8 Drawing Sheets

(56) References Cited

FOREIGN PATENT DOCUMENTS

| KR | 10-2013-0002922 A | 1/2013 |
|---|---|---|
| KR | 10-2013-0034503 A | 4/2013 |
| KR | 10-2013-0099509 A | 9/2013 |

OTHER PUBLICATIONS

Jinyoung Kwak et al., "Use of the self-assembly of tyrosine-containing bolaamphiphile molecules as a reactive template for metal deposition", Colloids and Surfaces B: Biointerfaces 102 (2013) 70-75.

* cited by examiner

METHOD FOR PREPARING ZINC-HISTIDINE SELF-ASSEMBLY BIOMIMETRIC COMPLEX, ZINC-HISTIDINE SELF-ASSEMBLY COMPLEX PREPARED BY SAID METHOD, AND METHOD FOR REDUCING CARBON DIOXIDE USING SAID ZINC-HISTIDINE SELF-ASSEMBLY COMPLEX

BACKGROUND OF THE INVENTION

1. Technical Field

The present invention relates to a method for preparing a zinc-histidine self-assembly biomimetic complex that activates a reaction to convert carbon dioxide into a bicarbonate ion, a zinc-histidine self-assembly biomimetic complex obtained by the preparation method, and a method for reducing carbon dioxide using the zinc-histidine self-assembly biomimetic complex.

2. Description of the Related Art

The energy we use is mostly obtained from the heat generated from the combustion of fossil fuels (e.g., petroleum, charcoal, natural gas, etc.) composed of hydrocarbons, but it cannot be acquired without emission of carbon dioxide. Carbon dioxide is a principal component constituting greenhouse gases and accounts for the greatest part of the greenhouse gas emissions.

The climate change caused by the greenhouse gases alters the natural environments of the Earth to raise the global sea level and unusual weather phenomena, such as local downpour, heavy snowstorm, and so forth, causing changes in the terrestrial and marine ecosystems. A bond of sympathy that the concentration of carbon dioxide in air among the gases of which the emission is controllable needs to be reduced to prevent the global warming is developing worldwide and a discussion about the method for reducing carbon dioxide is in progress.

In particular, according to the Kyoto Protocol created in Kyoto, Japan in 1997, the annexed agreement of the U.N. Convention on Climate Change (signed in 1992) specifies a code of conduct such as reduction of greenhouse gas emission aiming at easing the global warming. The Republic of Korea classified in the category of developing countries is exempt from the Kyoto Protocol, which requires nations to reduce their greenhouse gas emissions. But, it is expected that the demand for the reduction of greenhouse gas emissions is increasing in consideration of the tendency towards strengthening the related regulations as a result of the increase in the $CO_2$ emission in Korea and abroad and the current situation that Korea is one of the OECD-member countries emitting a lot of greenhouse gases.

The EU launched the EU emissions trading system (EU-ETS) of allowances for emitting carbon dioxide ($CO_2$) among the companies on Jan. 1, 2005 and began the second trading period among the countries in 2008. The EU-ETS set an upper limit on the total volume of $CO_2$ emissions for 13,000 installations having a generating unit of 20,000 Kw or above in the EU-zone and gave the individual power stations or industrial plants a permit to trade a surplus or shortage of the allowance according to their $CO_2$ emissions. The price of the emission allowance was around 7 to 8 euros per ton of $CO_2$ emissions and tended to rise as the due date for the target reduction of the $CO_2$ emission got closer. A failure to lower emissions resulted in a fine of 40 euros per ton of $CO_2$ emissions, and the fine was increased to 100 euros per ton of $CO_2$ emissions since 2008. The total quantity of the emission allowances to be traded in the EU emission market is estimated at approximately 2.1 billion tons a year, that is, a 10 billion euro a year business. It is expected that the company's purchasing cost for the $CO_2$ emission is going to soar in the future.

With such nationwide institutional demands and change, many studies on the $CO_2$ capture and conversion have been made. As for the $CO_2$ conversion, a variety of chemical conversion methods including inorganic catalysts are being developed and studies on the $CO_2$ capture and conversion using bio-proteins existent in nature are also actively in progress.

The advantage of the $CO_2$ conversion method using proteins and enzymes over the other methods using a catalyst based on inorganic substances is that the reaction takes place at ambient temperature and pressure. A representative example of the enzymes widely used for the $CO_2$ capture is carbonic anhydrase (hereinafter, referred to as "CA"), which CA can convert carbon dioxide into a bicarbonate ion.

In general, the conversion reaction from carbon dioxide to a bicarbonate ion is a kinetically very slow reaction. But, it is known that the organisms including mollusks that synthesize calcium carbonate can use the CA to accelerate the rate of such a reaction. The CA is also known to play a role in the physiological functions, such as respiration, ion transfer, acid-base control, etc. Therefore, the studies on the $CO_2$ capture using the CA are now in the spotlight.

Particularly, the activated site of the CA to convert $CO_2$ has a structure that three histidines surround the Zn ion at the center. The strength of the CA enzyme is that it can react with $10^4$ to $10^6$ $CO_2$ molecules per second in water and rapidly convert the $CO_2$ molecules into $HCO_3^-$.

Disadvantageously, however, the conventional carbonic anhydrase (CA) commercially available has a limitation in its large-scale production due to the difficulty in the duplication and purification process, involves high production cost and displays poor thermal stability, which is characteristic to enzymes. Thus there is an urgent demand for developing a substance as a substitute for the conventional CA.

PRIOR DOCUMENTS

Patent Documents

Korean Laid-Open Patent No. 2011-0087273
Korean Laid-Open Patent No. 2013-0034503
Korean Laid-Open Patent No. 2013-0002922
Korean Registration Patent No. 1163964

SUMMARY OF THE INVENTION

The present invention is to provide a novel self-assembly biomimetic complex having a function of converting carbon dioxide by synthesizing a novel amphiphilic substance containing histidyl imidazole and then causing a self-assembly process to prepare an enzyme-mimetic self-assembly complex having a similar structure to the activating site of a carbonic anhydrase.

The present invention is also to provide a method for reducing carbon dioxide with more economical feasibility and effectiveness by developing a novel self-assembly carbon dioxide reforming complex that can overcome the problems with the existing researches on the enzyme-related applications, such as high cost, poor thermal stability, etc., using the novel biomimetic self-assembly complex.

The method for preparing a carbonic anhydrase-mimetic self-assembly complex according to the present invention includes: (a) mixing L-histidine and p-toluene sulfonic acid in a first organic solvent to form a first mixed solution and recrystallizing the first mixed solution with ethyl ether to prepare a first mixed substance; (b) mixing the first mixed substance with azelaic acid in a second organic solvent to form a second mixed substance containing an imidazole group and an amide group; (c) mixing the second mixed substance with sodium hydroxide (NaOH) and hydrochloric acid (HCl) in a third organic solvent to form a third mixed solution and recrystallizing the third mixed solution with ethyl ether to prepare a third mixed substance having an amphiphilic characteristic; and (d) mixing the third mixed substance of the step (c) with an aqueous solution of a zinc precursor and causing a self-assembly to prepare a zinc-containing self-assembly biomimetic complex.

As used in the present invention, the first organic solvent is a mixture of benzyl alcohol and chloroform; the second organic solvent is a mixture of N,N-diisopropylethylamine (DIEA), n-hydroxysuccinimide (NMS), o-benzotriazole-N,N,N',N'-tetramethyl-uronium-hexafluoro-phosphate (HBTU), and dimethylformamide (DMF); and the third organic solvent is dimethylformamide (DMF).

Preferably, the step (a) is carried out at 80° C. for 12 hours; the step (b) is carried out at 25° C. for 2 to 6 hours; and the step (c) is carried out at 70° C. for 4 to 6 hours.

As intermediate substances in the preparation method of the present invention, the first mixed substance is histidine benzyl ester; the third mixed substance having an amphiphilic characteristic is histidine(His)-C7; and the zinc-containing self-assembly biomimetic complex of the step (d) is $(His)_m-Zn^{2+}-(H_2O)_n$, where m is 1, 2 or 3; and n is 0, 1 or 2.

Preferably, the concentration of histidine(His)-C7 used in the self-assembly step (d) is 2 to 4 mM and the concentration of the zinc precursor that is zinc chloride ($ZnCl_2$) is 0.01 to 10 mM.

In another embodiment of the present invention, there are provided a carbonic anhydrase-mimetic self-assembly complex prepared by the method for preparing a carbonic anhydrase-mimetic self-assembly composite, and a method for reducing carbon dioxide using the carbonic anhydrase-mimetic self-assembly complex to convert carbon dioxide into a bicarbonate ion.

DESCRIPTION OF THE PREFERRED EMBODIMENTS

The method for preparing a zinc-histidine complex (($His)_m-Zn^{2+}-(H_2O)_n$, where m is 1, 2 or 3; and n is 0, 1 or 2) of the present invention includes: (a) mixing L-histidine and p-toluene sulfonic acid in a first organic solvent to form a first mixed solution and recrystallizing the first mixed solution with ethyl ether to prepare a first mixed substance; (b) mixing the first mixed substance with azelaic acid in a second organic solvent to form a second mixed substance containing an imidazole group and an amide group; (c) mixing the second mixed substance with sodium hydroxide (NaOH) and hydrochloric acid (HCl) in a third organic solvent to form a third mixed solution and recrystallizing the third mixed solution with ethyl ether to prepare a third mixed substance having an amphiphilic characteristic; and (d) mixing the third mixed substance of the step (c) with an aqueous solution of a zinc precursor and causing a self-assembly to prepare a zinc-containing self-assembly biomimetic complex.

Mixing L-histidine and p-toluene sulfonic acid in the step (a) is carried out in the first organic solvent, and the first mixed solution thus obtained is recrystallized with ethyl ether to form the first mixed substance. Preferably, the first organic solvent is a mixture of benzyl alcohol and chloroform and the reaction is carried out at 80° C. for 12 hours.

The first mixed substance thus prepared in the step (a) is histidine benzyl ester.

Mixing the first mixed substance with azelaic acid in the step (b) is preferably carried out in the second organic solvent at the room temperature of 25° C. for about 2 to 6 hours. The second organic solvent is preferably a mixture of N,N-diisopropylethylamine (DIEA), n-hydroxysuccinimide (NHS), o-benzotriazole-N,N,N',N'-tetramethyl-uronium-hexafluoro-phosphate (HBTU), and dimethylformamide (DMF).

The step (c) of mixing the second mixed substance with NaOH and HCl to produce the third mixed substance having an amphiphilic characteristic is carried out in dimethylformamide (DMF) used as the organic solvent at 70° C. for 4 to 6 hours. Then, a recrystallization with ethyl ether is performed to form the third mixed substance. In this regard, the third mixed substance is histidine(His)-C7. Between the steps (c) and (d) may be further included a step of drying the third mixed substance. The drying step is preferably carried out at 35° C. for about 24 hours.

Figure 1:
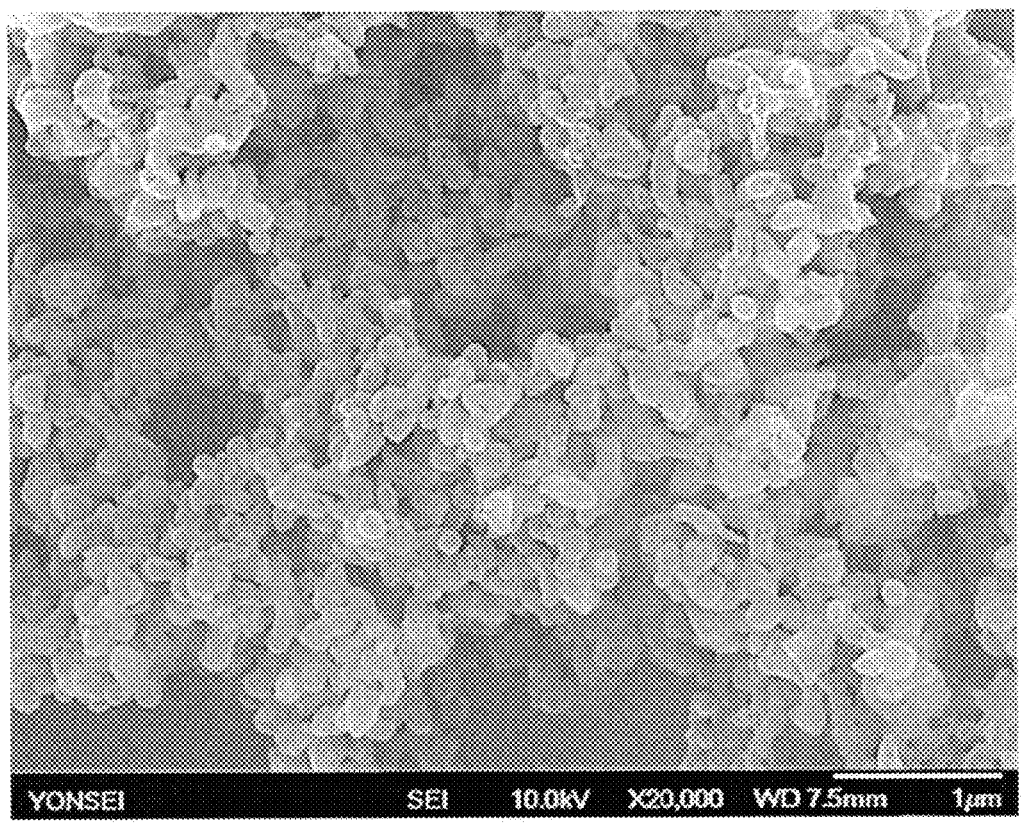
FIG. 1 is an SEM image of a zinc-histidine self-assembly biomimetic complex of the present invention.

The self-assembly process of the step (d) uses histidine (His)-C7 of 2 to 4 mM and a zinc precursor, zinc chloride, of 0.01 to 10 mM to form a zinc-containing self-assembly biomimetic complex represented by $(His)_m-Zn^{2+}-(H_2O)_n$, where m is 1, 2 or 3; and n is 0, 1 or 2. FIG. 1 presents an SEM image of the zinc-histidine self-assembly biomimetic complex of the present invention On the other hand, the method for reducing carbon dioxide according to another embodiment of the present invention is to convert carbon dioxide into a bicarbonate ion using the zinc-histidine self-assembly biomimetic complex obtained by the preparation method as a catalyst.

The zinc-histidine self-assembly biomimetic complex of the present invention has a catalytic activity high enough to replace the existing carbonic anhydrase.

The reaction to convert carbon dioxide into a bicarbonate ion is represented by the following chemical mechanisms:

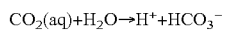

$$CO_2(aq) + H_2O \rightarrow H^+ + HCO_3^-$$

The zinc-histidine self-assembly biomimetic complex of the present invention functions as a catalyst in the reaction and has an effect to increase the reaction rate of the reaction.

Hereinafter, the present invention will be described in further detail with reference to Examples as well as the accompanying drawings, which are given to exemplify the present invention for specific explanation and not intended to limit the scope of the present invention.

EXAMPLE 1

Figure 2:
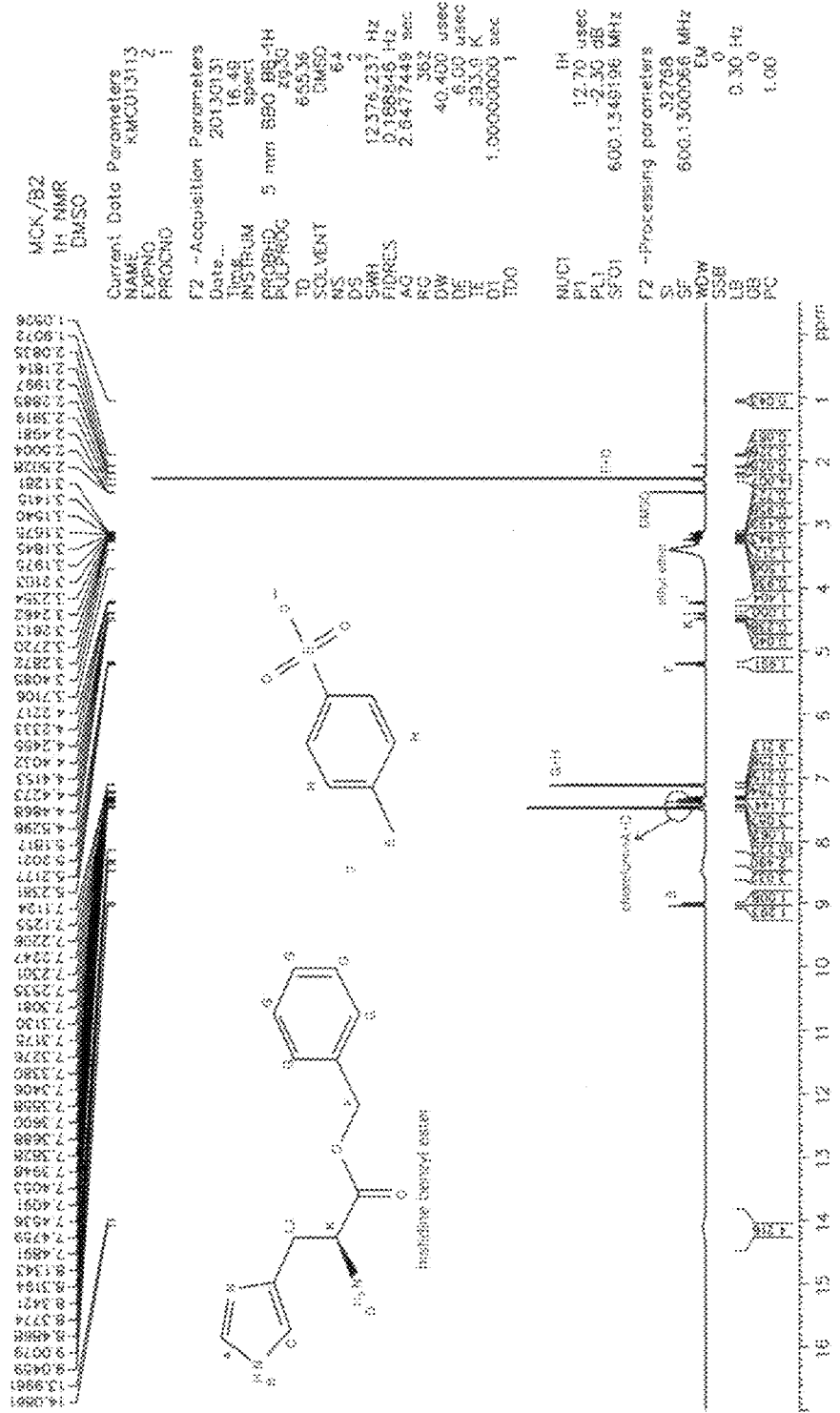
FIG. 2 shows the H-NMR results of the first mixed substance of the present invention.
Figure 3:
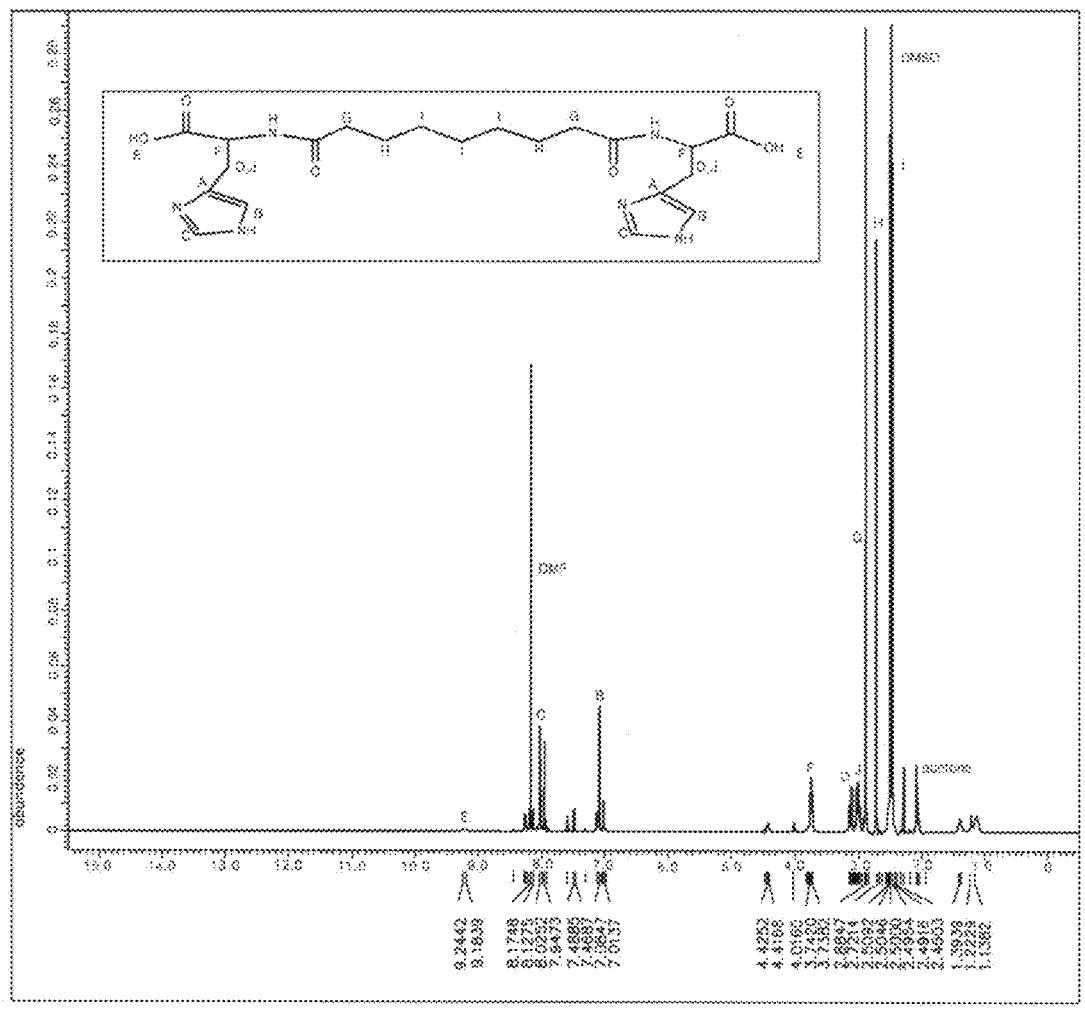
FIG. 3 shows the H-NMR results of the third mixed substance of the present invention.

L-histidine powder and a solution of p-toluene sulfonic acid are mixed together and then added to benzyl alcohol and chloroform to cause a reaction at 80° C. for 12 hours. Then, ethyl ether is added to cause recrystallization to form a first mixed substance. The first mixed substance thus obtained is subjected to H-NMR analysis to demonstrate the occurrence of the reaction. As can be seen in FIG. 2, the first mixed substance that is an intermediate product of the present invention is histidine benzyl ester.

After dried out sufficiently, 10 g of the first mixed substance is taken and mixed with azelaic acid, HBTU, DIEA, and NHS in dimethyl form amide at the room temperature for 4 hours to prepare a second mixed solution, which is then subjected to recrystallization to obtain a second mixed substance.

The second mixed substance thus obtained is mixed with DMF and NaOH to cause a reaction at 80° C. After addition of HCl, the mixture is removed of the solvent through rotary evaporation to obtain a third mixed substance that is an amphiphilic complex having an amide group and an imidazole group. The third mixed substance is then subjected to a H-NMR structural analysis and proved to be histidine(His)-C7 having a carboxyl group at either end and seven carbon atoms at the center.

EXAMPLE 2

The amphiphilic complex, histidine(His)-C7, as obtained in Example 1 is dried out at 35° C. for about 24 hours. The histidine (His)-C7 dried out is mixed with $ZnCl_2$ that is a zinc precursor in an aqueous solution and subjected to self-assembly. In this regard, the concentrations of histidine (His)-C7 and $ZnCl_2$ are 3 mM and 1 mM, respectively. The aqueous solution of the zinc-histidine self-assembly complex thus prepared is used in the subsequent Examples to evaluate the conversion activity for carbon dioxide ($CO_2$) and the conversion rate of carbon dioxide ($CO_2$) into a bicarbonate ion.

EXAMPLE 3

Evaluation on Conversion Activity for Carbon Dioxide

An evaluation on the conversion activity for carbon dioxide is conducted in order to examine the performance of the zinc-histidine self-assembly complex of the present invention. As the carbonic anhydrase has a characteristic to convert p-nitrophenyl acetate (p-NPA) into p-nitrophenol, the conversion activity for carbon dioxide is evaluated by way of the indirect activity measurement method that involves observing how much the p-nitrophenyl acetate (p-NPA) is converted into p-nitrophenol. Such an indirect measurement method uses the UV/VIS spectrophotometer to measure the degree of conversion for p-nitrophenyl acetate into p-nitrophenol.

2 ml of p-NPA and 1 ml of the zinc-histidine self-assembly complex are added to a mixed solution containing 1 ml of acetonitrile and 9 ml of distilled water. Then, the change of absorbance is measured for 5 minutes using the UV/VIS spectrophotometer at 400 nm that is the specific wavelength for the phenol group. The experimental procedures are performed in the same manner as described above while the pH value of the aqueous solution of the zinc-histidine self-assembly complex is varied to 7, 8, or 9, so that the degree of conversion is reduced to the reaction rate constant. The measurement results are presented in FIG. 4.

Figure 4:
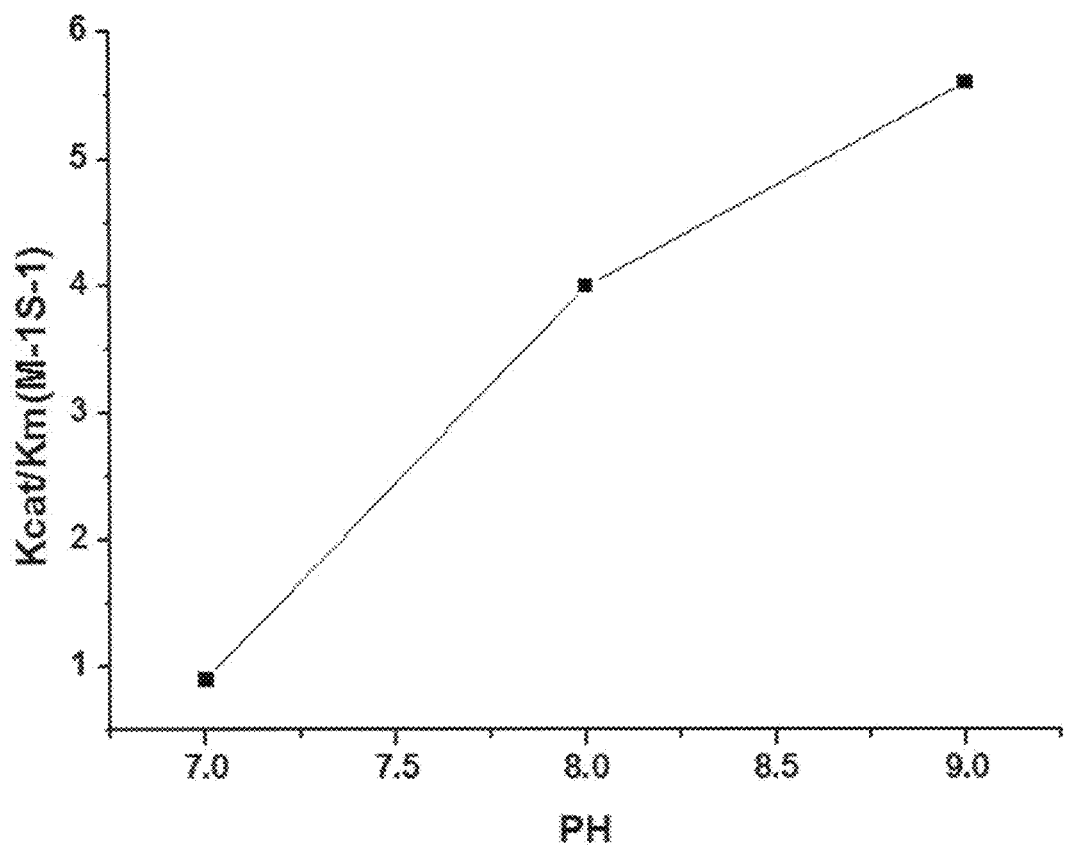
FIG. 4 shows the measurement results of the reaction rate constant (Kcat/Km) as a function of the pH change of the zinc-histidine self-assembly biomimetic complex.

As can be seen from FIG. 4, the conversion rate of p-NPA increases in the alkaline region rather than in the neutral region. It is similarly expected that the conversion of carbon dioxide is achieved more effectively in the alkaline region.

EXAMPLE 4

Evaluation of Thermal Stability

Figure 5:
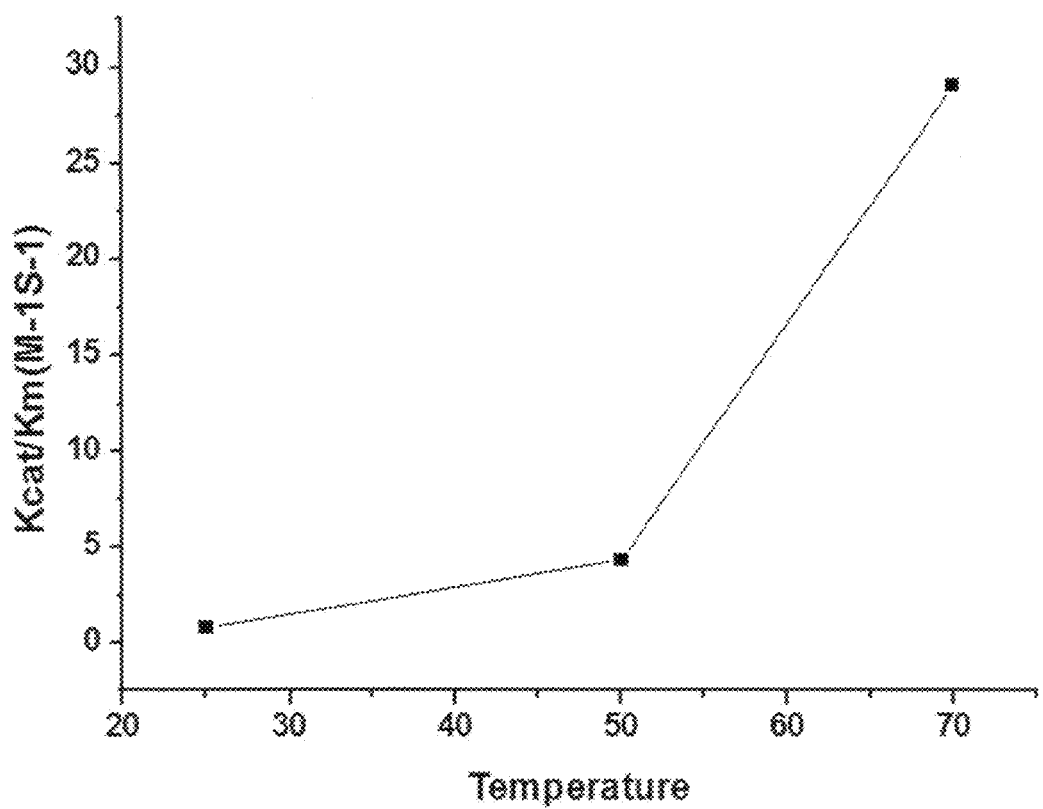
FIG. 5 shows the measurement results of the reaction rate constant (Kcat/Km) as a function of the temperature change (25° C., 50° C., 70° C.) of the zinc-histidine self-assembly biomimetic complex at pH 7.
Figure 6:
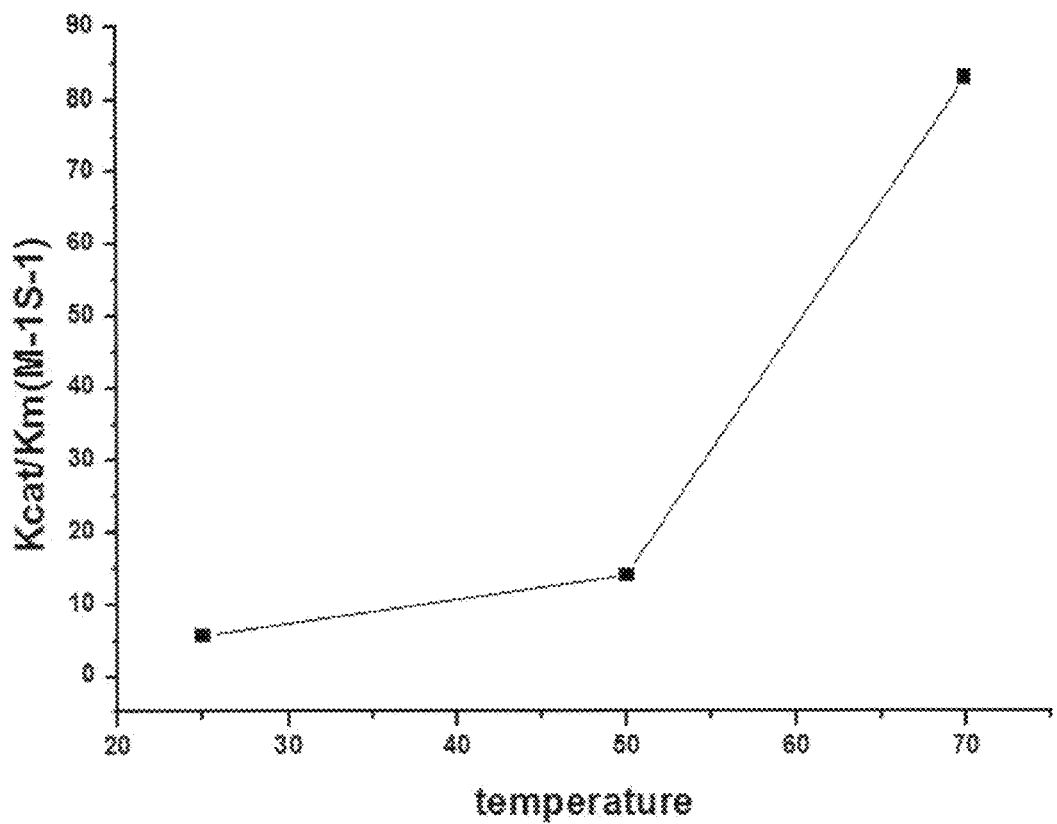
FIG. 6 shows the measurement results of the reaction rate constant (Kcat/Km) as a function of the temperature change (25° C., 50° C., 70° C.) of the zinc-histidine self-assembly biomimetic complex at ph 9.

The procedures are performed in the same manner as described in Example 3, excepting that the temperature is increased to the room temperature, 50° C., and 70° C., to measure the change of the reaction rate constant in each case. The measurement results at pH 7 and pH 9 are presented in FIGS. 5 and 6, respectively. It can be seen that the present invention secures a considerably high thermal stability at high temperature to overcome the problem with the existing carbonic anhydrase and shows the reaction rate enhanced with an increase in the temperature.

EXAMPLE 5

Measurement of Conversion Rate for $CO_2$ into Bicarbonate Ion in Water

The measurement is conducted in regards to the degree of conversion for the carbon dioxide dissolved in water into $HCO_3^-$ by the zinc-histidine self-assembly complex of the present invention. As the pH value lowers with the conversion of carbon dioxide dissolved in water into $HCO_3^-$, the degree of conversion of carbon dioxide into $HCO_3^-$ in water can be determined by measuring the variation of pH using the in-time pH meter.

25 ml of the aqueous solution containing the zinc-histidine(His)-C7 self-assembly complex of the present invention is agitated for about 10 seconds, and an aqueous solution containing 33 mM of $CO_2$ is added to the resultant solution, during which the change of pH is measured in real time. The procedures are performed in the same manner as described above, excepting that the pH value of the aqueous solution containing the zinc-histidine self-assembly complex is varied to 7, 8, or 9 using NaOH or citric acid. The measurement results in regards to the change of pH are presented in FIG. 7.

In addition, the procedures are performed in the same manner as described above, excepting that the change of pH is measured while the concentration of $CO_2$ dissolved in the aqueous solution is 33 mM, 22 mM, or 11 mM. The measurement results are presented in FIG. 8.

Figure 7:
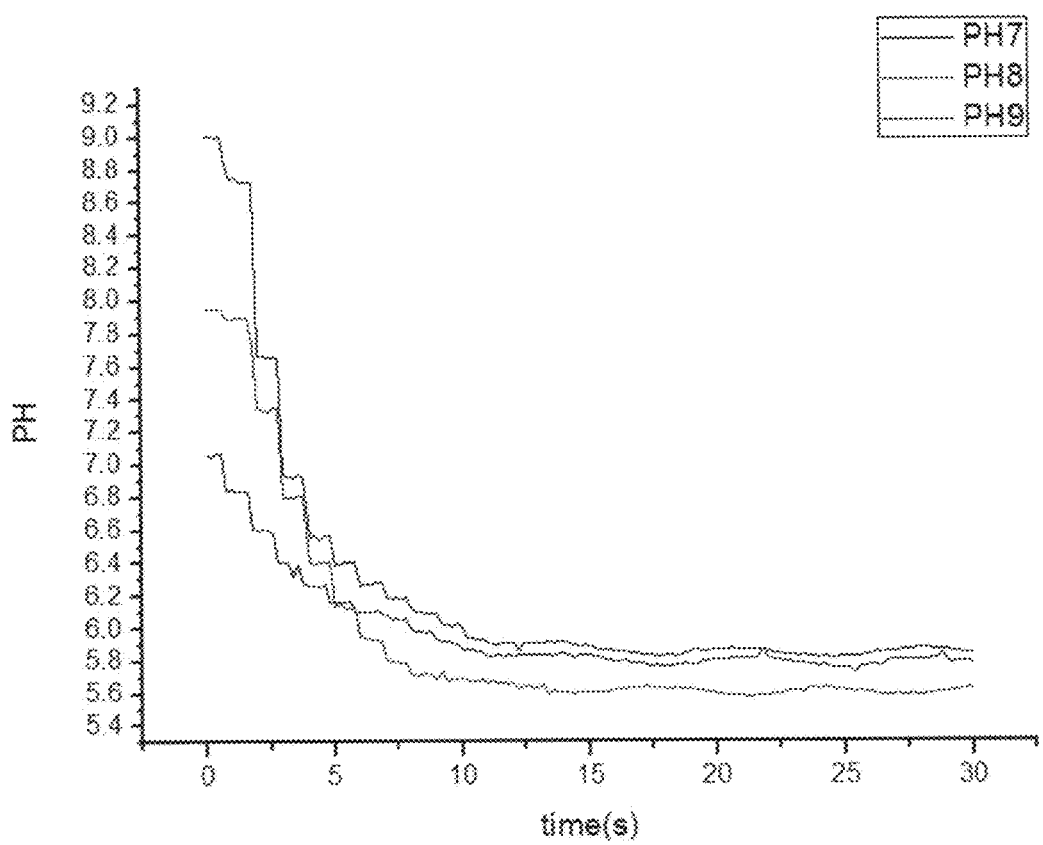
FIG. 7 is the measurement results in regards to the pH change as a function of time as the zinc-histidine self-assembly biomimetic complex is fed into an aqueous solution containing $CO_2$.
Figure 8:
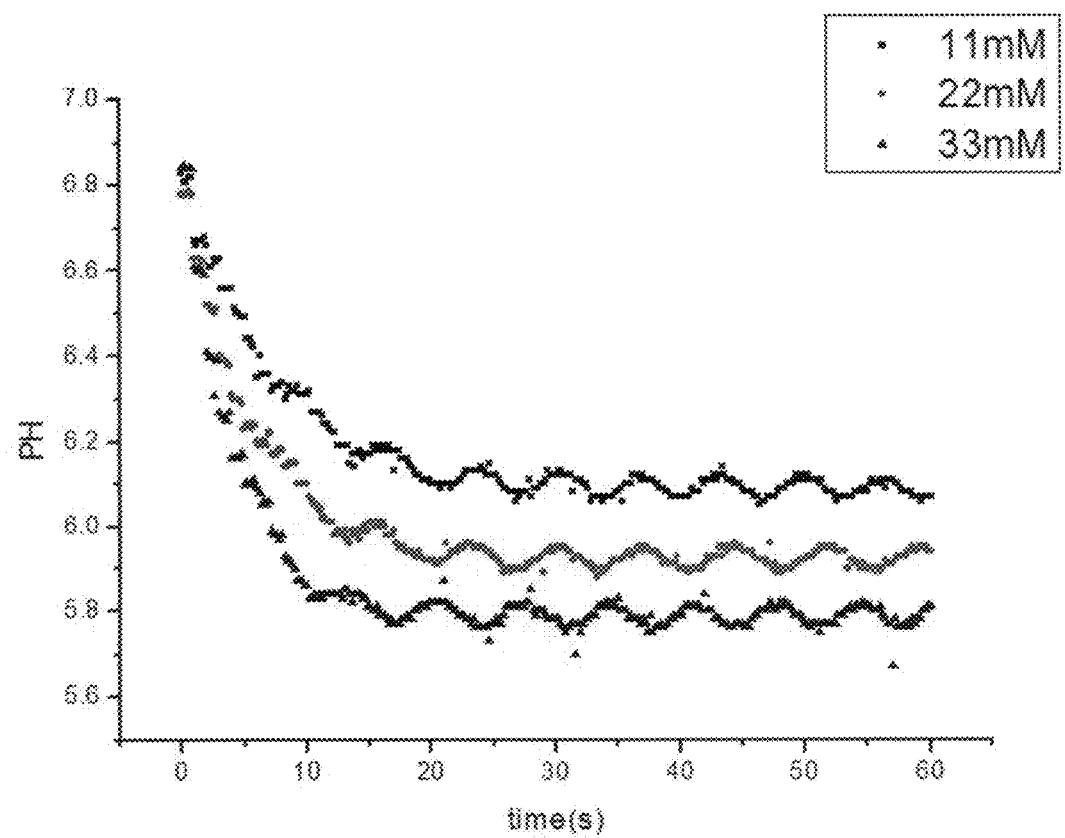
FIG. 8 is the measurement results in regards to the pH change as a function of time as the zinc-histidine self-assembly biomimetic complex is fed into aqueous solutions containing $CO_2$ dissolved at different concentrations (11 mM, 22 mM, 33 mM).

As can be seen from the results of FIGS. 7 and 8, the zinc-histidine self-assembly complex of the present invention not only has a remarkably high activity on the conversion of carbon dioxide but also displays excellences in thermal stability and storage stability.

As described above, the preparation method for the carbonic anhydrase-mimetic self-assembly complex of the present invention can be used to replace the conventional carbonic anhydrase and widely used in the process for reducing emission of greenhouse gases due to its excellences in thermal stability and ability of converting carbon dioxide.

The present invention can prepare a zinc-histidine self-assembly biomimetic complex imitating carbonic anhydrase and a catalyst for accelerating a conversion of carbon dioxide into a bicarbonate ion and reduce the emission of carbon dioxide using the zinc-histidine self-assembly composite obtained by the preparation method of the present invention.

In addition, the present invention can replace a carbonic anhydrase that is expensive to secure the economical feasibility of the technique for reducing carbon dioxide and has benefits for commercialization due to excellences in thermal stability and storage stability.

What is claimed is:

1. A method for preparing a carbonic anhydrase-mimetic self-assembly complex, comprising:
   (a) mixing L-histidine and p-toluene sulfonic acid in a first organic solvent to form a first mixed solution and recrystallizing the first mixed solution with ethyl ether to prepare a first mixed substance;
   (b) mixing the first mixed substance with azelaic acid in a second organic solvent to form a second mixed substance containing an imidazole group and an amide group;
   (c) mixing the second mixed substance with sodium hydroxide (NaOH) and hydrochloric acid (HCl) in a third organic solvent to form a third mixed solution and recrystallizing the third mixed solution with ethyl ether to prepare a third mixed substance having an amphiphilic characteristic; and
   (d) mixing the third mixed substance of the step (c) with an aqueous solution of a zinc precursor and causing a self-assembly to prepare a zinc-containing self-assembly biomimetic complex.

2. The method as claimed in claim 1, wherein the first organic solvent is a mixture of benzyl alcohol and chloroform.

3. The method as claimed in claim 1, wherein the step (a) is carried out at 80° C. for 12 hours.

4. The method as claimed in claim 1, wherein the first mixed substance is histidine benzyl ester.

5. The method as claimed in claim 1, wherein the second organic solvent is a mixture of N,N-diisopropylethylamine (DIEA), n-hydroxysuccinimide (NHS), o-benzotriazole-N,N,N',N'-tetramethyl-uronium-hexafluoro-phosphate (HBTU), and dimethylformamide (DMF).

6. The method as claimed in claim 1, wherein the step (b) is carried out at 25° C. for 2 to 6 hours.

7. The method as claimed in claim 1, wherein the step (c) is carried out at 70° C. for 4 to 6 hours.

8. The method as claimed in claim 1, wherein the third mixed substance having an amphiphilic characteristic is histidine(His)-C7.

9. The method as claimed in claim 1, wherein the zinc-containing self-assembly biomimetic complex of the step (d) is $(His)_m$-$Zn^{2+}$—$(H_2O)_n$, wherein m is 1, 2 or 3; and n is 0, 1 or 2.

10. The method as claimed in claim 8, wherein in the self-assembly step (d), the concentration of histidine(His)-C7 is 2 to 4 mM and the concentration of the zinc precursor is 0.01 to 10 mM.

11. The method as claimed in claim 10, wherein the zinc precursor is zinc chloride ($ZnCl_2$).

* * * * *